United States Patent
Coulson et al.

(12)

(10) Patent No.: US 6,313,318 B1
(45) Date of Patent: *Nov. 6, 2001

(54) PROCESS FOR THE PREPARATION OF α-METHYLENE LACTONES

(75) Inventors: Dale Robert Coulson; Leo E. Manzer, both of Wilmington; Norman Herron, Newark, all of DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/528,632

(22) Filed: Mar. 20, 2000

Related U.S. Application Data

(60) Provisional application No. 60/126,883, filed on Mar. 30, 1999, and provisional application No. 60/126,884, filed on Mar. 30, 1999.

(51) Int. Cl.[7] .................. C07D 313/00; C07D 309/00
(52) U.S. Cl. .................. 549/266; 549/273; 549/295
(58) Field of Search .................. 549/266, 273, 549/295

(56) References Cited

U.S. PATENT DOCUMENTS 5,166,357  11/1992  Orlek et al. .................. 514/299

FOREIGN PATENT DOCUMENTS

| 0295553 A1 | 6/1988 | (EP) . |
| 0366304 A2 | 10/1989 | (EP) . |
| 10-120672 | 5/1998 | (JP) . |
| 10298172 | 11/1998 | (JP) . |

OTHER PUBLICATIONS

Watts et al., J. Chem. Soc. Chem. Comm. 27 (1970).
A. W. Murray et al., Synthesis, Jan. 1985, pp. 35–38.
J. MARTIN, A New Method for the Synthesis of alpha–Methylenebutyrolactones, Chemical Communications, 1970, 27, Dow Chemical Company, Eastern Research Laboratory, Wayland, Massachusetts.

*Primary Examiner*—Amelia Owens
(74) *Attorney, Agent, or Firm*—Inna Y. Belopolsky

(57) ABSTRACT

This invention concerns a process for the addition of formaldehyde to the α carbon atom of lactones for the production of α-methylenelactones, and specifically α-methylene-γ-butyrolactone.

27 Claims, No Drawings

PROCESS FOR THE PREPARATION OF α-METHYLENE LACTONES

This application claims the benefit of U.S. Provisional Application No. 60/126,883 filed Mar. 30, 1999 and U.S. Provisional Application No. 60/126,884, filed Mar. 30, 1999.

FIELD OF THE INVENTION

This invention concerns a process for the addition of formaldehyde to the α carbon atom of lactones to produce α-methylenelactones, and specifically α-methylene-γ-butyrolactone.

TECHNICAL BACKGROUND

α-Methylene-γ-butyrolactone is useful as a monomer in the preparation of both homopolymers and copolymers.

An early synthesis of α-methylene-γ-butyrolactone involved two steps (Watts et al., *J. Chem. Soc. Chem. Comm.* 27 (1970)). The first is carboxylation of γ-butyrolactone with methyl methoxymagnesium carbonate (Stiles' reagent) to produce the acid. Next, the acid is briefly treated with a mixture of aqueous formaldehyde and diethylamine, followed by a separate treatment of the crude product with sodium acetate in acetic acid. The first step requires 6–7 hours and affords almost quantitative yields, whereas the second step can be accomplished in less than 30 minutes but with yields of only 50%.

A. W. Murray et al. *Synthesis,* January 1985, p 35–38 report the development of a two-step route to α-methylene-γ-butyrolactone that consists of the reaction of γ-butyrolactone with ethyl formate in the presence of sodium hydride base followed by the isolation of the resulting formyl derivative as its sodium salt and subsequent reaction with an aldehyde. B. S. Orlek et al., U.S. Pat. No. 5,166,357, use this same route specifying the use of formaldehyde as the aldehyde.

Although the above methods for the production of α-methylene lactones are useful, they are time consuming and are multipart processes. The instant invention represents an advance in the art as it is a single step process that produces the desired product in high yields and good selectivity.

SUMMARY OF THE INVENTION

The invention provides a process for preparing α-methylenelactones of Formula II comprising heating lactones of Formula I and formaldehyde in the vapor phase at a temperature of above 200° C. in the presence of a basic catalyst:

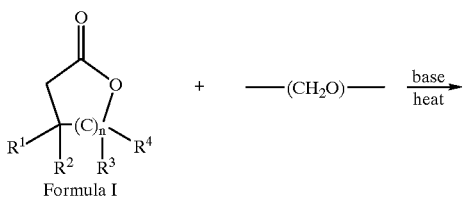

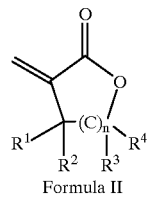

wherein,
n=1–11;
$R^1$, $R^2$, $R^3$, and $R^4$ taken independently are hydrogen, hydrocarbyl or substituted hydrocarbyl, $C_1$–$C_{18}$ unsubstituted or substituted alkyl, unsubstituted or substituted alkenyl, unsubstituted or substituted cycloalkyl, unsubstituted or substituted cycloalkyl containing at least one heteroatom, unsubstituted or substituted aromatic ring, and unsubstituted or substituted aromatic ring containing at least one heteroatom. In a specific embodiment the lactone of Formula I is γ-butyrolactone and the α-methylenelactone of Formula II is α-methylene-γ-butyrolactone.

Catalysts suitable in the present invention may be selected from the group consisting of metal oxides, metal hydroxides, and metal carbonates and may be supported or unsupported and may make use of catalyst promoters.

Additionally the invention provides a process for preparing α-methylenelactones of Formula II comprising:
(a) heating lactones of Formula I and formaldehyde in the vapor phase at a temperature of above 200° C. in the presence of a basic catalyst for a time sufficient for the α-methylenelactones of Formula II to be formed;

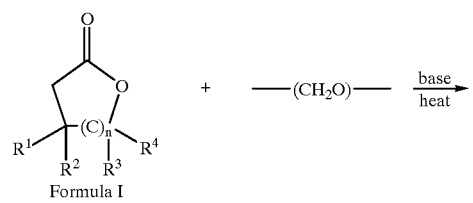

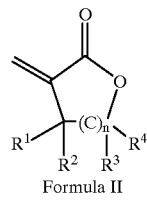

wherein,
n=1–11;
$R^1$, $R^2$, $R^3$, and $R^4$ taken independently are hydrogen, hydrocarbyl or substituted hydrocarbyl, $C_1$–$C_{18}$ unsubstituted or substituted alkyl, unsubstituted or substituted alkenyl, unsubstituted or substituted cycloalkyl, unsubstituted or substituted cycloalkyl containing at least one heteroatom, unsubstituted or substituted aromatic ring, and unsubstituted or substituted aromatic ring containing at least one heteroatom;
(b) separating the lactones of Formula I from the basic catalyst;
(c) contacting the basic catalyst with oxygen for a time sufficient to permit catalyst regeneration; and
(d) repeating steps (a) through (c).

Additionally the invention provides process for preparing α-methylenelactones of Formula II comprising:

(a) heating lactones of Formula I and formaldehyde in the vapor phase at a temperature of above 200° C. in the presence of a basic catalyst for a time sufficient for the α-methylenelactones of Formula II to be formed in a reactor effluent;

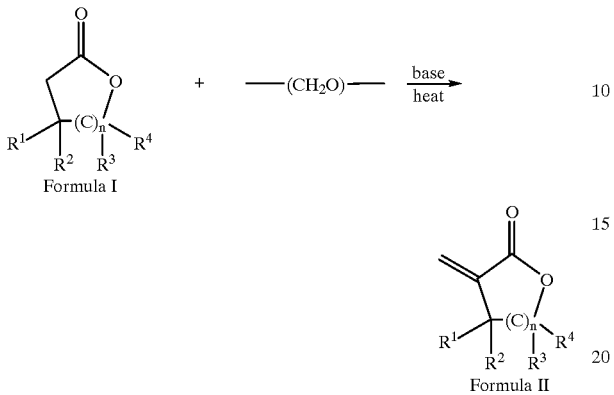

Formula I

Formula II wherein, n=1–11;

$R^1$, $R^2$, $R^3$ and $R^4$ taken independently are hydrogen, hydrocarbyl or substituted hydrocarbyl, $C_1$–$C_{18}$ unsubstituted or substituted alkyl, unsubstituted or substituted alkenyl, unsubstituted or substituted cycloalkyl, unsubstituted or substituted cycloalkyl containing at least one heteroatom, unsubstituted or substituted aromatic ring, and unsubstituted or substituted aromatic ring containing at least one heteroatom, (b) collecting the reactor effluent of step (a); and (c) contacting the collected effluent with the base catalyst at a temperature of above 200° C.

DETAILED DESCRIPTION OF THE INVENTION

The process of the present invention concerns an efficient methenylation of lactones to yield α-methylenelactones of which α-methylene-γ-butyrolactone is a preferred member. The reaction proceeds according to the general scheme:

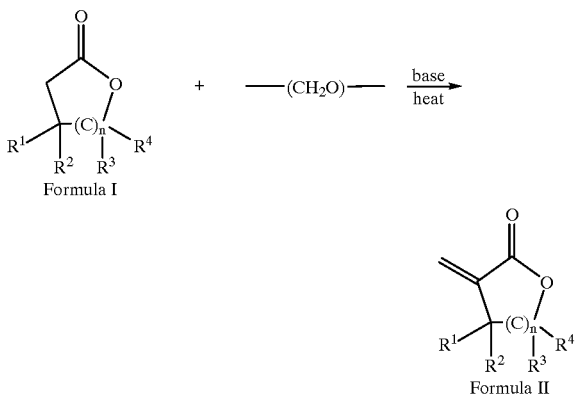

Formula I

Formula II wherein, n=1–11;

$R^1$, $R^2$, $R^3$, and $R^4$ taken independently are hydrogen, hydrocarbyl or substituted hydrocarbyl, $C_1$–$C_{18}$ unsubstituted or substituted alkyl, unsubstituted or substituted alkenyl, unsubstituted or substituted cycloalkyl, unsubstituted or substituted cycloalkyl containing at least one heteroatom, unsubstituted or substituted aromatic ring, and unsubstituted or substituted aromatic ring containing at least one heteroatom. In a specific embodiment the lactone of Formula I is γ-butyrolactone and the α-methylenelactone of Formula II is α-methylene-γ-butyrolactone. $R^1$, $R^2$, $R^3$, and $R^4$ may join to form members of a ring structure selected from the group consisting of, unsubstituted or substituted cycloalkyl, unsubstituted or substituted cycloalkyl containing at least one heteroatom in the ring, unsubstituted or substituted aromatic ring, and unsubstituted or substituted aromatic ring containing at least one heteroatom in the ring. Most preferred compounds are where the lactone of Formula I is γ-butyrolactone and the α-methylenelactone of Formula II is α-methylene-γ-butyrolactone.

In the context of this disclosure, a number of terms and abbreviations shall be utilized. The following definitions are provided.

When a group contains a substituent which can be hydrogen, for example $R^1$, $R^2$, $R^3$, and $R^4$ then, when this substituent is taken as hydrogen, it is recognized that this is equivalent to said group being unsubstituted.

The term "alkyl" includes straight-chain or branched alkyl, such as, methyl, ethyl, n-propyl, i-propyl, or the different butyl, pentyl and hexyl isomers. Also included are all isomers up to and including octadecane.

A "hydrocarbyl group" is a univalent group containing only carbon and hydrogen. If not otherwise stated, it is preferred that hydrocarbyl groups herein contain 1 to about 30 carbon atoms.

By "substituted hydrocarbyl" herein is meant a hydrocarbyl group which contains one or more substituent groups which are inert under the process conditions to which the compound containing these groups is subjected. The substituent groups also do not substantially interfere with the process. If not otherwise stated, it is preferred that substituted hydrocarbyl groups herein contain 1 to about 30 carbon atoms. Included in the meaning of "substituted" are heteroaromatic rings.

One of skill in the art will know where and how to obtain the α-methylenelactones reactant of the present invention. For example γ-butyrolactone is readily available from commercial sources such as Aldrich Chemical Company (Millwaukee, Wis.).

The process of the present invention is carried out in the vapor state, at temperatures greater than 200° C., over highly basic catalysts. Although any temperature above 200° C. is useful, temperature in the range of about 250° C. to about 400° C. are preferred where ranges of about 300° C. to about 340° C. are most preferred. In one preferred embodiment the lactone and formaldehyde of the present invention are in the vapor phase.

The basic catalysts are selected from the metal oxides, hydroxides, and carbonates. The oxides, hydroxides and carbonates employed herein may be used as powders, granules, or other particulate forms, or may be supported on an essentially inert support as is common in the art of catalysis. Representative catalysts include but are not limited to of magnesium oxide, barium oxide, barium hydroxide, lanthanum oxide potassium hydroxide, cadmium oxide, rubidium oxide, lithium hydroxide, strontium hydroxide, sodium hydroxide, calcium hydroxide, barium carbonate and mixtures thereof. Preferred catalysts are barium hydroxide and lanthanum oxide, where barium hydroxide is most preferred.

In some cases reaction conditions may result in the decrease of catalytic efficiency. In these situations it may be useful to modify the reaction process to allow for catalyst regeneration. For example, contacting the present catalysts with $O_2$ at elevated temperatures has the effect of reactivating the catalyst. Contact temperatures with $O_2$ may range from about 300° C. to about 500° C. where temperatures of about 400° C. to about 425° C. are preferred.

The metal oxide, hydroxide and carbonate catalysts of the present invention may further comprise catalyst additives and promoters which will enhance the efficiency of the catalyst. Use of theses materials are common and well known in the art (see for example, *Kirk-Othmer Encyclopedia of Chemical Technology*, Howe-Grant Ed., Vol. 5, pp 326–346, (1993), John Wiley & Sons, New York and *Ullmann's Encyclopedia of Industrial Chemistry*, Vol. A5, Gerhartz et al., Eds., pp. 337–346, (1986), VCH Publishers, New York, both hereby incorporated by reference.) Particularly useful in the present invention is gold used as a promoter with $BA(OH)_2$.

Basic catalysts of the present invention may be supported or unsupported. Where a support is desired suitable supports include but are not limited to silica, titania, zirconia, alumina, carbon, various zeolites and mixtures thereof. Particularly suitable catalyst—support combinations include barium hydroxide and lanthanum oxide supported on $SiO_2$.

Preferred catalysts of the present invention have been effective in producing product at good selectivities. Selectivities of greater than 50% are typical where selectivities of greater than 95% are common.

It will be appreciated that the selectivities and yields of product may be enhanced by additional contact with the catalyst. For example, yields and selectivities may be increase where the reactor effluent containing a mixture of reactant and product may be passed one or more times over the catalyst under the reaction conditions to enhance the conversion of reactant to product.

One component of the invention is formaldehyde. Formaldehyde may be supplied in a variety of forms including as a solution or in the form of a formaldehyde polymer. Polymers of formaldehyde are more generally denominated polyacetals and include or are characterized by a linear polymer chain containing recurring —($CH_2O$)— units or ggroups. A convenient form of formaldehyde was formalin, (37% aqueous formaldehyde).

The desired products, including α-methylene-γ-butyrolactone, are recovered using techniques common to the art. For example, when allowed to cool the α-methylene-γ-butyrolactone reaction mixture forms a viscous, clear mass. Alternatively, when heated under vacuum, the α-methylene-γ-butyrolactone/γ-butyrolactone mixture can be distilled directly from the reaction mixture. Additionally, the reaction mixture can be dissolved in water, adjusted to pH=4 with 6N HCl, then distilled. Similarly, the separation of α-methylene-γ-butyrolactone from γ-butyrolactone can be accomplished using vacuum distillation with a spinning band column. Another method to recover the desired product is to polymerize α-methylene-γ-butyrolactone in the γ-butyrolactone solution using standard free-radical polymerization, isolate the polymer by precipitation from methanol, then thermally depolymerize back to α-methylene-γ-butyrolactone by heating under vacuum. Finally, α-methylene-γ-butyrolactone may also be separated from -γ-butyrolactone by melt crystallization.

Table 1 summarizes the results of Examples 1–29. Of the catalysts tested $Ca(OH)_2/SiO_2$, $NaOH/SiO_2$, $LiOH/SiO_2$, $Sr(OH)_2/SiO_2$, $KOH/SiO_2$ and $Ba(OH)_2/SiO_2$ gave yields exceeding 5%. The best overall catalyst was 8 wt % $Ba(OH)_2/SiO_2$ which gave an 11% yield of α-methylene-γ-butyrolactone at 37% conversion of the γ-butyrolactone (37% product selectivity) at 340° C. No significant amounts of other volatile compounds were noted.

As seen from Table 1, the base oxides or hydroxides of Mg, Ca, Sr and Ba (Group IIA) are active catalysts. Similarly, the base oxides or hydroxides of Na, K and Rb(in combination with Mg) (Group IA) are active catalysts. These Groups include the most basic metal oxides known. Most of these materials were tested as deposited on an oxide support.

The support material need not have a special character except that it should be stable to the reaction conditions. Metal oxides of Groups IVB and higher, up to Group IVA, are preferable. Rare earth oxides are also acceptable. It is believed that a support is preferred in order to maintain high catalyst surface areas.

Table 2 shows examples (30–34) wherein feed ratios are varied. The most significant improvement in the % selectivities to α-methylene-γ-butyrolactone came from variations in the reactant feed ratio. When the feed ratio was increased from 1:1 to 1:8 (lactone:formaldehyde) the average % yield increased as the ratio of formaldehyde increased.

Table 3 shows results with the varied catalysts and conditions. Example 37 identifies LiOH/Silica as an especially useful catalysts/support combination. Table 4 shows the formation of α-methylene-γ-butyrolactone and γ-methylene-γ-butyrolactone using preferred catalyst ($LaO/SiO_2$) under varied conditions. Example 46 (Table 5) shows the ability to regenerate the catalyst $Ba(OH)_2/SiO_2$ with air. Example 47 (Table 6) illustrates that there is enhanced conversion of γ-butyrolactone to α-methylene butyrolactone if the reactor effluent is recycled across the catalyst a second time, indicating that a recycled procedure improves product yield.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

Common reagents were purchased from Sigma-Aldrich and solvents from VWR Scientific.

The meaning of abbreviations is as follows: "µL" means microliter, "mL" means milliliter(s), "L" means liter(s), "mM" means millimolar, "M" means molar, "mmol" means millimole(s) and "ng" means nanogram(s).

Reaction of γ-butyrolactone with Formaldehyde

Solutions containing γ-butyrolactone in formalin (37% aqueous formaldehyde) at various feed ratios, was fed to a vaporizer (held at 200° C.) followed by the introduction of a gas ($N_2$) to carry the vapor through a ¼ inch tubular reactor containing a catalyst heated to the appropriate reaction temperature. A series of basic materials (1–2 g samples) was examined for catalytic activity by exposing these materials to the test conditions for about 0.25 to about 6 hr periods. In all cases, ca. 25% to 75% extents of conversion of the γ-butyrolactone were found, depending upon the catalyst employed.

The Tables 1–6 contains the examples and show catalyst, nature and amount, feed ratio of γ-butyrolactone to formalin, temperature, flow rate, observed conversion and yield or selectivity.

Below are listed the preparations of the catalysts listed in the table.

$KOH/SiO_2$ 5 g of granular, sol-gel derived silica (+8 mesh; 300 $m^2g^{-1}$) was slurried into a solution of 1 g KOH in 10 mL distilled water. The slurry was stirred for 10 minutes and then evaporated to dryness. The recovered solid was dried in a gold boat under flowing (100 mL/min) nitrogen at 550° C. for 2 hours and then collected under nitrogen as a granular white solid.

$Ba(OH)_2/SiO_2$ 5 g of granular, sol-gel derived silica (+8 mesh; 300 $m^2g^{-1}$) was slurried into a solution of 1 g $Ba(OH)_2$ octahydrate in 10 mL distilled water. The slurry was stirred for 10 minutes and then evaporated to dryness. The recovered solid was dried in a gold boat under flowing (100 mL/min) nitrogen at 550° C. for 2 hours and then collected under nitrogen as a granular white solid.

$CdO/SiO_2$ 5 g of granular, sol-gel derived silica (+8 mesh; 300 $m^2g^{-1}$) was slurried into a solution of 1 g $Cd(NO_3)_2$ tetrahydrate in 10 mL distilled water. The slurry was stirred for 10 minutes and then evaporated to dryness. The recovered solid was dried in a gold boat under flowing (100 mL/min) nitrogen at 550° C. for 2 hours and then collected under nitrogen as a granular brown solid.

8% $Ba(OH)_2/SiO_2$ 50 g of granular, sol-gel derived silica (+8 mesh; 300 $m^2g^{-1}$) was slurried into a solution of 10 g $Ba(OH)_2$ octahydrate in 100 mL distilled water. The slurry was stirred for 10 minutes and then evaporated to dryness. The recovered solid was dried in a gold boat under flowing (100 mL/min) nitrogen at 550° C. for 2 hours and then collected under nitrogen as a granular white solid.

1% $Ba(OH)_2/SiO_2$ 10 g of granular, sol-gel derived silica (+8 mesh; 300 $m^2g^{-1}$) was slurried into a solution of 0.2 g $Ba(OH)_2$ octahydrate in 20 mL distilled water. The slurry was stirred for 10 minutes and then evaporated to dryness. The recovered solid was dried in a gold boat under flowing (100 mL/min) nitrogen at 550° C. for 2 hours and then collected under nitrogen as a granular white solid.

10% $Ba(OH)_2/\gamma$-$Al_2O_3$ 10 g of γ-alumina powder (150 $m^2g^{-1}$) was slurried into a solution of 2 g $Ba(OH)_2$ octahydrate in 20 mL distilled water. The slurry was stirred for 10 minutes and then evaporated to dryness. The recovered solid was dried in a gold boat under flowing (100 mL/min) nitrogen at 550° C. for 2 hours and then collected under nitrogen as a granular white solid.

$Ba(OH)_2/TiO_2$ 10 g of titania (anatase) powder (~30 $m^2g^{-1}$) was slurried into a solution of 2 g $Ba(OH)_2$ octahydrate in 20 mL distilled water. The slurry was stirred for 10 minutes and evaporated to dryness. The recovered solid was dried in a gold boat under flowing (100 mL/min) nitrogen at 550° C. for 2 hours and then collected under nitrogen as a granular white solid.

10% $Ba(OH)_2/MgO$ 10 g of magnesia powder (~10 $m^2g^{-1}$) was slurried into a solution of 2 g $Ba(OH)_2$ octahydrate in 20 mL distilled water. The slurry was stirred for 10 minutes and then evaporated to dryness. The recovered solid was dried in a gold boat under flowing (100 mL/min) nitrogen at 550° C. for 2 hours and then collected under nitrogen as a granular white solid.

10% $Ba(OH)_2/ZrO_2$ 10 g of zirconia powder (~25 $m^2g^{-1}$) was slurried into a solution of 2 g $Ba(OH)_2$ octahydrate in 20 mL distilled water. The slurry was stirred for 10 minutes and then evaporated to dryness. The recovered solid was dried in a gold boat under flowing (100 mL/min) nitrogen at 550° C. for 2 hours and then collected under nitrogen as a granular white solid.

10% $Ba(OH)_2/SiO_2/Al_2O_3$ 10 g of silica-alumina powder (~150 $m^2g^{-1}$) was slurried into a solution of 2 g $Ba(OH)_2$ octahydrate in 20 mL distilled water. The slurry was stirred for 10 minutes and then evaporated to dryness. The recovered solid was dried in a gold boat under flowing (100 mL/min) nitrogen at 550° C. for 2 hours and then collected under nitrogen as a granular white solid.

$Ca(OH)_2/SiO_2$ 10 g of silica granules (~300 $m^2g^{-1}$) was slurried into a solution of 0.25 g $Ca(OH)_2$ in 100 mL distilled water. The slurry was stirred for 10 minutes and then evaporated to dryness. The recovered solid was dried in a gold boat under flowing (100 mL/min) nitrogen at 550° C. for 2 hours and then collected under nitrogen as a granular white solid. ICP revealed 1.15 wt % Ca in this sample.

$Sr(OH)_2/SiO_2$ 10 g of silica granules (~300 $m^2g^{-1}$) was slurried into a solution of 0.25 g $Sr(OH)_2$ octahydrate in 100 mL distilled water. The slurry was stirred for 10 minutes and then evaporated to dryness. The recovered solid was dried in a gold boat under flowing (100 mL/min) nitrogen at 550° C. for 2 hours and then collected under nitrogen as a granular white solid. ICP revealed 0.60 wt % Sr in this sample.

$NaOH/SiO_2$ 10 g of silica granules (~300 $m^2g^{-1}$) was slurried into a solution of 0.25 g NaOH in 20 mL distilled water. The slurry was stirred for 10 minutes and then evaporated to dryness. The recovered solid was dried in a gold boat under flowing (100 mL/min) nitrogen at 550° C. for 2 hours and then collected under nitrogen as a granular white solid. ICP revealed 1.45 wt % Na in this sample.

$LiOH/SiO_2$ 10 g of silica granules (~300 $m^2g^{-1}$) was slurried into a solution of 0.25 g LiOH in 20 mL distilled water. The slurry was stirred for 10 minutes and then evaporated to dryness. The recovered solid was dried in a gold boat under flowing (100 mL/min) nitrogen at 550° C. for 2 hours and then collected under nitrogen as a granular white solid. ICP revealed 0.42 wt % Li in this sample.

10% $Ba(OH)_2/SiO_2$

In a 100 ml round bottom flask, 25 ml of a solution of 1.86 wt % Ba (as the hydroxide) in $H_2O$ were combined with 5.0 grams of silica gel (Grace Davison, grade 57, 10–20 mesh). The slurry was stirred at room temperature for 10 minutes. The $H_2O$ was then removed by rotovac. The solid was calcined at 550° C. for 2 hours in flowing nitrogen.

10% $Ba(OH)_2/1\% Au/SiO_2$

In a 100 ml round bottom flask, 25 ml of a solution of 1.86% Ba (as the hydroxide) in $H_2O$ were combined with 1.18 grams of 0.3 molar gold chloride in $H_2O$ and 5.0 grams of silica gel. The slurry was stirred at room temperature for 10 minutes. The $H_2O$ was then rotovac removed. The solid was calcined at 550° C. for 2 hours in flowing nitrogen.

TABLE 1

Effects of Basic Catalysts on Condensation of γ-Butyrolactone with Formaldehyde

| Example No. | Catalyst (Repeats) | Catalyst wt, g | Feed Wt. Ratio[a] | T, °C. | Conditions | % Conv[b] | % Yield[c] |
|---|---|---|---|---|---|---|---|
| 1 | MgO | 2.0 | 1:1 | 380 | 12 cc/min $N_2$ 0.5 cc/h liq feed 6 h runtime | 24 | 1.4 |
| 2 | MgO | 2.0 | 1:1 | 380 | 12 cc/min $N_2$ 0.5 cc/h liq feed 6 h runtime | 19 | 1.5 |
| 3 | MgO | 2.0 | 1:1 | 340 | 12 cc/min $N_2$ 0.5 cc/h liq feed 6 h runtime | 31 | 2.1 |
| 4 | MgO | 2.0 | 1:1 | 340 | 12 cc/min $N_2$ 0.5 cc/h liq feed 6 h runtime | 30 | 2.1 |
| 5 | $Ba(OH)_2/SiO_2$ | 1.0 | 1:1 | 340 | 12 cc/min $N_2$ 0.5 cc/h liq feed 6 h runtime | 36 | 14 |
| 6 | $Ba(OH)_2/SiO_2$ | 1.0 | 1:1 | 370 | 12 cc/min $N_2$ 0.5 cc/h liq feed 6 h runtime | 36 | 14 |
| 7 | $KOH/SiO_2$ | 0.80 | 1:1 | 340 | 12 cc/min $N_2$ 0.5 cc/h liq feed 6 h runtime | 37 | 5.8 |
| 8 | $CdO/SiO_2$ | 1.0 | 1:1 | 340 | 12 cc/min $N_2$ 0.5 cc/h liq feed 6 h runtime | 34 | 3.0 |
| 9 | $RbO_{0.01}MgO_{0.99}$ | 1.0 | 1:1 | 340 | 12 cc/min $N_2$ 0.5 cc/h liq feed 6 h runtime | 11 | 0.12 |
| 10 | LYCOS2—Naz | 1.0 | 1:1 | 340 | 12 cc/min $N_2$ 0.5 cc/h liq feed 6 h runtime | 46 | 0.01 |
| 11 | $RbO_{0.05}MgO_{0.95}$ | 0.89 | 1:1 | 340 | 12 cc/min $N_2$ 0.5 cc/h liq feed 6 h runtime | 32 | 1.7 |
| 12 | H-Beta | 1.0 | 1:1 | 340 | 12 cc/min $N_2$ 0.5 cc/h liq feed 6 h runtime | 25 | 0.21 |
| 13 | LZ-20 | 2.0 | 1:1 | 340 | 12 cc/min $N_2$ 0.5 cc/h liq feed 6 h runtime | 69 | 1.1 |
| 14 | Mg-ZSM-5 | 2.0 | 1:1 | 340 | 12 cc/min $N_2$ 0.5 cc/h liq feed 6 h runtime | 70 | 1.9 |
| 15 | $LiOH/SiO_2$ | 1.0 | 1:1 | 340 | 12 cc/min $N_2$ 0.5 cc/h liq feed 6 h runtime | 37 | 14 |
| 16 | $SrOH/SiO_2$ | 1.0 | 1:1 | 340 | 12 cc/min $N_2$ 0.5 cc/h liq feed 6 h runtime | 21 | 10 |
| 17 | $NaOH/SiO_2$ | 1.0 | 1:1 | 340 | 12 cc/min $N_2$ 0.5 cc/h liq feed 6 h runtime | 24 | 9 |
| 18 | $Ca(OH)_2/SiO_2$ | 1.0 | 1:1 | 340 | 12 cc/min $N_2$ 0.5 cc/h liq feed 6 h runtime | 32 | 11 |
| 19 | 8% $Ba(OH)_2/SiO_2$ (1)[§] | 1.0 | 1:1 | 340 | 12 cc/min $N_2$ 0.5 cc/h liq feed 6 h runtime | 64 | 6.0 |
| 19a | 8% $Ba(OH)_2/SiO_2$ (2)[§] | 1.0 | 1:1 | 340 | 12 cc/min $N_2$ 0.5 cc/h liq feed 6 h runtime | 63 | 6.0 |
| 19b | 8% $Ba(OH)_2/SiO_2$ (3)[§] | 1.0 | 1:1 | 340 | 12 cc/min $N_2$ 0.5 cc/h liq feed 6 h runtime | 48 | 7.4 |
| 19c | 8% $Ba(OH)_2/SiO_2$ (4)[§] | 1.0 | 1:1 | 340 | 12 cc/min $N_2$ 0.5 cc/h liq feed 6 h runtime | 35 | 7.6 |
| 19d | 8% $Ba(OH)_2/SiO_2$ (5)[§] | 1.0 | 1:1 | 340 | 12 cc/min $N_2$ 0.5 cc/h liq feed 6 h runtime | 65 | 4.5 |
| 20 | 8% $Ba(OH)_2/SiO_2$ | 1.0 | 1:1 | 340 | 5 cc/min $N_2$ 0.5 cc/h liq feed 6 h runtime | 48 | 9.9 |
| 21 | 8% $Ba(OH)_2/SiO_2$ | 1.0 | 1:2 | 340 | 12 cc/min $N_2$ 0.5 cc/h liq feed | 41 | 17 |

TABLE 1-continued

Effects of Basic Catalysts on Condensation of γ-Butyrolactone with Formaldehyde

| Example No. | Catalyst (Repeats) | Catalyst wt, g | Feed Wt. Ratio[a] | T, °C. | Conditions | % Conv[b] | % Yield[c] |
|---|---|---|---|---|---|---|---|
| 21a | 8% Ba(OH)$_2$/SiO$_2$ (2)§ | 1.0 | 1:2 | 340 | 6 h runtime 12 cc/min N$_2$ 0.5 cc/h liq feed | 48 | 14 |
| 22 | 8% Ba(OH)$_2$/SiO$_2$ | 1.0 | 1:2 | 340 | 6 h runtime 12 cc/min N$_2$ 0.5 cc/h liq feed | 48 | 16 |
| 23 | Ba(OH)$_2$/SiO$_2$/Al$_2$O$_3$ | 1.0 | 1:2 | 340 | 6 h runtime 12 cc/min N$_2$ 0.5 cc/h liq feed | 35 | 6.6 |
| 24 | Ba(OH)$_2$/TiO$_2$ | 2.0 | 1:1 | 340 | 6 h runtime 12 cc/min N$_2$ 0.5 cc/h liq feed | 25 | 2.5 |
| 25 | 10% Ba(OH)$_2$/ZrO$_2$ | 3.0 | 1:1 | 340 | 6 h runtime 12 cc/min N$_2$ 0.5 cc/h liq feed | 20 | 2.1 |
| 26 | 10% Ba(OH)$_2$/γ-Al$_2$O$_3$ | 1.5 | 1:1 | 340 | 6 h runtime 12 cc/min N$_2$ 0.5 cc/h liq feed | 32 | 4.5 |
| 27 | 10% Ba(OH)$_2$/MgO | 1.5 | 1:1 | 340 | 6 h runtime 12 cc/min N$_2$ 0.5 cc/h liq feed | 25 | 1.5 |
| 28 | 1% Ba(OH)$_2$/SiO$_2$ | 1.0 | 1:1 | 340 | 6 h runtime 12 cc/min N$_2$ 0.5 cc/h liq feed | 44 | 10.4 |
| 29 | Ba(OH)$_2$/SiO$_2$ | 1.0 | 1:4 | 340 | 6 h runtime 12 cc/min N$_2$ 0.5 cc/h liq feed | 38 | 22 |

[a]Feed wt. Ratio = Wt of γ-butyrolactone: Wt. of formalin (37%) (1:1 wt ratio = 0.945 mole ratio)
[b]% Conversion = (Moles of γ-butyrolactone converted/moles of γ-butyrolactone fed)*100
[c]% Yield = (Moles of α-methylene butyrolactone formed/Moles of γ-butyrolactone converted)*100
§Parenthetical numbers indicate duplicate (repeats) runs

TABLE 2

Effects of Changes in Reactant Ratios on Condensation of γ-Butyrolactone with Formaldehyde (4.0 g of Ba(OH)$_2$/SiO$_2$)

| Example No. | Feed Wt. Ratio[a] | T, °C. | Conditions | % Conv[b] | % Yield[c] |
|---|---|---|---|---|---|
| 30 | 1:1 | 340 | 24 cc/min N$_2$ 1.0 cc/h liq feed 6 h runtime | 36 | 15 |
| 31 | 1:2 | 340 | 24 cc/min N$_2$ 1.0 cc/h liq feed 6 h runtime | 34 | 18 |
| 32 | 1:4 | 340 | 24 cc/min N$_2$ 1.0 cc/h liq feed 6 h runtime | 44 | 19 |
| 33 | 1:4 | 340 | 24 cc/min N$_2$ 1.0 cc/h liq feed 6 h runtime | 41 | 20 |
| 34 | 1:8 | 340 | 24 cc/min N$_2$ 1.0 cc/h liq feed 6 h runtime | 35 | 30 |

[a]Feed wt. Ratio = Wt of γ-butyrolactone: Wt. of formalin (37%) (1:1 wt ratio = 0.945 mole ratio)
[b]Conversion = (Moles of γ-butyrolactone converted/moles of γ-butyrolactone fed)* 100
[c]% Yield = (Moles of α-methylene butyrolactone formed/Moles of γ-butyrolactone converted)* 100

TABLE 3

| Example No. | Catalyst (Repeats) | Catalyst wt, g | Feed Molar Ratio (Formaldehyde:GBL) | T, °C. | Conditions | % Conv[b] | % Selectivity |
|---|---|---|---|---|---|---|---|
| 35 | 10% LaO/SiO$_2$ | 1 | 8 | 320 | 24 cc/min N$_2$ 1 cc/h liq feed | 16.0 | >95 |

TABLE 3-continued

| Example No. | Catalyst (Repeats) | Catalyst wt, g | Feed Molar Ratio (Formaldehyde: GBL) | T, °C. | Conditions | % Conv[b] | % Selectivity |
|---|---|---|---|---|---|---|---|
| 36 | 10% La$_2$O$_3$/SiO$_2$ | 1 | 8 | 380 | 0.25 h runtime 24 cc/min N$_2$ 1 cc/h liq feed | 36.7 | >95 |
| 37 | 0.42% LiOH/SiO$_2$ | 1 | 8 |  | 0.25 h runtime 24 cc/min N$_2$ 1 cc/h liq feed | 53.3 | >95 |
| 38 | 10% Ba(OH)$_2$/Subunit Carbon | 1 | 8 | 340 | 0.25 h runtime 24 cc/min N$_2$ 1 cc/h liq feed | 9.73 | >95 |
| 39 | 10% Ba(OH)$_2$/1% Au/SiO$_2$ | 1 | 8 | 250 | 0.25 h runtime 24 cc/min N$_2$ 1 cc/h liq feed | 18.8 | >95 |
| 40 | 10% Ba(OH)$_2$/1% Au/SiO$_2$ | 1 | 8 | 280 | 0.25 h runtime 24 cc/min N$_2$ 1 cc/h liq feed | 53.5 | >95 |
| 41 | 10% Ba(OH)$_2$/1% Au/SiO$_2$ | 1 | 8 | 320 | 0.25 h runtime 24 cc/min N$_2$ 1 cc/h liq feed | 36.9 | >95 |

[a]Molar Feed Ratio = Moles of formaldehyde: moles of γ-butyrolactone (Formaldehyde used as 37 wt % aqueous solution
[b]% Conversion = (Moles of γ-butyrolactone converted/moles of γ-butyrolactone fed)* 100

TABLE 4

Conversion of γ-methyl-γ-Butyrolactone to α-methylene-α-methyl-γ-butyrolactone over 10% LaO/SiO$_2$

| Example No. | Catalyst | Catalyst wt, g | Feed Molar Ratio (Formaldehyde: Me-GBL) | T, °C. | Conditions | % Conv[b] | % Selectivity to Me-MBL |
|---|---|---|---|---|---|---|---|
| 42 | 10% LaO/SiO$_2$ | 2 | 8 | 340 | 48 cc/min N$_2$ 1 cc/h liq feed 0.25 h runtime | 40.1 | >95% |
| 43 | 10% LaO/SiO$_2$ | 2 | 8 | 340 | 48 cc/min N$_2$ 1 cc/h liq feed 1 h runtime | 23 | >95% |
| 44 | 10% LaO/SiO$_2$ | 2 | 8 | 300 | 48 cc/min N$_2$ 1 cc/h liq feed 1 h runtime | 33.9 | >95% |
| 45 | 10% LaO/SiO$_2$ | 1 | 8 | 340 | 24 cc/min N$_2$ 1 cc/h liq feed 0.25 h runtime | 57.7 | >95% |

[a] Molar Feed Ratio = Moles of formaldehyde: moles of γ-butyrolactone (Formaldehyde used as 37 wt % aqueous solution)
[b] Conversion = (Moles of γ-butyrolactone converted/moles of γ-butyrolactone fed)*100

TABLE 5

Example 46
Reaction Of Formalin With Butyrolactone,
Showing Effect Of Cyclic Regeneration With Air Under Varied Conditions

| Regeneration[§] Cycle | Catalyst | Catalyst wt, g | Feed Molar Ratio (Formaldehyde: Me-GBL) | T, °C. | Conditions | % Conv[b] | % Selectivity |
|---|---|---|---|---|---|---|---|
| 1 | 10% Ba(OH)$_2$/SiO$_2$ | 1 | 8 | 340 | 48 cc/min N$_2$ 1 cc/h liq feed 0.25 h runtime | 36.0 | >95 |
|  | 10% Ba(OH)$_2$/SiO$_2$ | 1 | 8 | 340 | 48 cc/min N$_2$ 1 cc/h liq feed 1 h runtime | 23.4 | >95 |
| 2 | 10% Ba(OH)$_2$/SiO$_2$ | 1 | 8 | 340 | 48 cc/min N$_2$ 1 cc/h liq feed 0.25 h runtime | 34.9 | >95 |
|  | 10% Ba(OH)$_2$/SiO$_2$ | 1 | 8 | 340 | 48 cc/min N$_2$ 1 cc/h liq feed | 25.00 | >95 |

TABLE 5-continued

Example 46
Reaction Of Formalin With Butyrolactone,
Showing Effect Of Cyclic Regeneration With Air Under Varied Conditions

| Regeneration[§] Cycle | Catalyst | Catalyst wt, g | Feed Molar Ratio (Formaldehyde: Me-GBL) | T, °C. | Conditions | % Conv[b] | % Selectivity |
|---|---|---|---|---|---|---|---|
| 3 | 10% Ba(OH)$_2$/SiO$_2$ | 1 | 8 | 340 | 1 h runtime 48 cc/min N$_2$ 1 cc/h liq feed | 35.8 | >95 |
|   | 10% Ba(OH)$_2$/SiO$_2$ | 1 | 8 | 340 | 0.25 h runtime 48 cc/min N$_2$ 1 cc/h liq feed | 22.6 | >95 |
| 4 | 10% Ba(OH)$_2$/SiO$_2$ | 1 | 8 | 340 | 1 h runtime 48 cc/min N$_2$ 1 cc/h liq feed | 34.0 | >95 |
|   | 10% Ba(OH)$_2$/SiO$_2$ | 1 | 8 | 340 | 0.25 h runtime 48 cc/min N$_2$ 1 cc/h liq feed 1 h runtime | 21.9 | >95 |

TABLE 6

Example 47
Demonstration of Enhanced Conversion of GBL to MBL after recycling

| Catalyst | Cat Vol (cc) | Feed Molar Ratio | Feed cc/hr | N2 ccm | CT (s) | TOS (h) | Rctr Temp (C.) | GBL/MBL Molar Ratio after Rx | Norm % GBL conv |
|---|---|---|---|---|---|---|---|---|---|
| BaO/1%Au/SiO$_2$ | 2 | 8:1 | 2 | 48 | 1.5 | 0.25 | 340 | 0.55 | 28.6 |

Example 47 illustrates that the conversion of γ-butyrolactone (GBL) to α-methylene butyrolactone (MBL) is enhanced if the reactor effluent is recyceld a second time through the reactor containing the catalyst. As is seen in the table above, the molar ratio of GBL/MBL drops from 1 to 0.55 after a second exposure to the catalyst under reaction conditions, indicating further conversion of GBL to MBL.

What is claimed is:

1. A process for preparing α-methylenelactones of Formula II comprising heating lactones of Formula I and formaldehyde in the vapor phase at a temperature of above 200° C. in the presence of a basic catalyst:

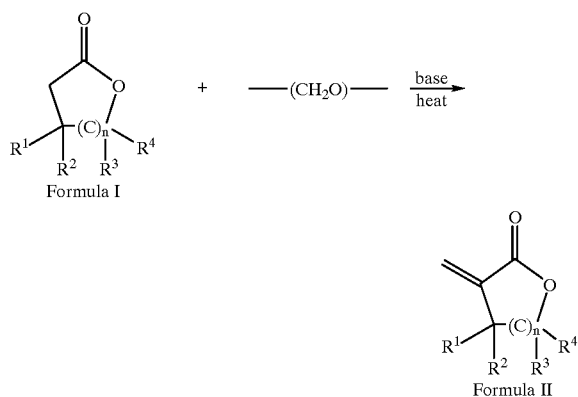

wherein, n=1–11;

R$^1$, R$^2$, R$^3$ and R$^4$ taken independently are hydrogen, C$_1$–C$_{30}$ unsubstituted or substituted alkyl, unsubstituted or substituted alkenyl, unsubstituted or substituted cycloalkyl, unsubstituted or substituted cycloalkyl containing at least one heteroatom unsubstituted or substituted aromatic ring, and unsubstituted or substituted aromatic ring containing at least one heteroatom.

2. A process according to claim 1 wherein R$^1$, R$^2$, R$^3$ and, R$^4$ are joined to form members of a ring structure selected from the group consisting of unsubstituted or substituted cycloalkyl, unsubstituted or substituted cycloalkyl containing at least one heteroatom in the ring unsubstituted or substituted aromatic ring, and unsubstituted or substituted aromatic ring containing at least one heteroatom in the ring.

3. The process of claims 1 or 2 wherein the lactone of Formula I is γ-butyrolactone and the α-methylenelactone of Formula II is α-methylene-γ-butyrolactone.

4. The process of claim 1 or 2 wherein R$^3$ is CH$_3$.

5. A process according to claim 1 wherein the temperature is from about 250° C. to about 400° C.

6. A process according to claim 5 wherein the temperature is from about 300° C. to about 340° C.

7. A process according to claim 1 wherein the base catalyst is selected from the group consisting of metal oxides, metal hydroxides, and metal carbonates.

8. A process according to claim 7 wherein the base catalyst is selected from the group consisting of magnesium oxide, barium hydroxide, barium oxide, lanthanum oxide potassium hydroxide, cadmium oxide, rubidium oxide, lithium hydroxide, strontium hydroxide, sodium hydroxide, calcium hydroxide, barium carbonate and mixtures thereof.

9. A process according to claim 7 wherein the base catalyst is optionally supported on a suitable support.

10. A process according to claim 7 wherein the base catalyst optionally comprises a catalyst promoter.

11. A process according to claim 10 wherein said catalyst promoter is gold.

12. A process according to claim 9 wherein the suitable support is selected from the group consisting of silica, titania, zirconia, alumina, carbon, zeolites and mixtures thereof.

13. A process according to claim 9 wherein the base catalyst is selected from the group consisting of magnesium oxide, barium hydroxide, barium oxide, lanthanum oxide, potassium hydroxide, cadmium oxide, rubidium oxide, lithium hydroxide, strontium hydroxide, sodium hydroxide, barium carbonate, calcium hydroxide, and wherein the suitable support is $SiO_2$.

14. A process according to claim 8 wherein the α-methylenelactone is produced at a selectivity of at least 50%.

15. A process according to claim 14 wherein the α-methylenelactone is produced at a selectivity of at least 95%.

16. A process according to claim 13 wherein the supported catalyst is $Ba(OH)_2/SiO_2$.

17. A process according to claim 13 wherein the supported catalyst is $La(OH)_2/SiO_2$.

18. A process according to claim 12 wherein the supported catalyst is $Ba(OH)_2/Carbon$.

19. A process according to claim 11 wherein the supported catalyst is $Ba(OH)_2/Au/SiO_2$.

20. A process according to claim 1 wherein the formaldehyde is in the form of formalin.

21. A process according to claim 1 wherein the formaldehyde is provided in a form selected from the group consisting of formaldehyde polymer, actals and polyacetals.

22. A process for preparing α-methylenelactones of Formula II comprising:
(a) heating lactones of Formula I and formaldehyde in the vapor phase at a temperature of above 200° C. in the presence of a basic catalyst for a time sufficient for the α-methylenelactones of Formula II to be formed;

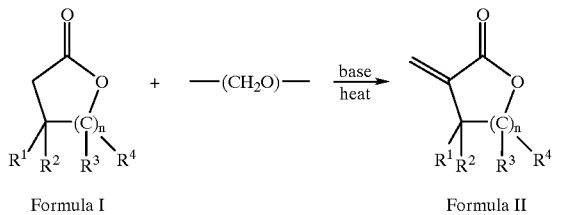

Formula I          Formula II wherein,
n=1–11;
$R^1$, $R^2$, $R^3$ and $R^4$ taken independently are hydrogen, $C_1$–$C_{30}$ unsubstituted or substituted alkyl, unsubstituted or substituted alkenyl, unsubstituted or substituted cycloalkyl, unsubstituted or substituted cycloalkyl containing at least one heteroatom, unsubstituted or substituted aromatic ring, and unsubstituted or substituted aromatic ring containing at least one heteroatom,
(b) separating the lactones of Formula I from the basic catalyst;
(c) contacting the basic catalyst with oxygen for a time sufficient to permit catalyst regeneration; and
(d) repeating steps (a) through (c).

23. A process according to claim 22 wherein the contacting of the basic catalyst with oxygen of step (c) is for a time of about 5 min to about 60 min.

24. A process according to claim 22 wherein the contacting of the basic catalyst with oxygen of step (c) is at a temperature of about 300° C. to about 500° C.

25. A process according to claim 24 wherein the contacting of the basic catalyst with oxygen of step (c) is at a temperature of about 400° C. to about 425° C.

26. A process for preparing α-methylenelactones of Formula II comprising:
(a) heating lactones of Formula I and formaldehyde in the vapor phase at a temperature of above 200° C. in the presence of a basic catalyst for a time sufficient for the α-methylenelactones of Formula II to be formed in a reactor effluent;

Formula I          Formula II wherein,
n=1–11;
$R^1$, $R^2$, $R^3$ and $R^4$ taken independently are hydrogen, $C_1$–$C_{30}$ unsubstituted or substituted alkyl, unsubstituted or substituted alkenyl, unsubstituted or substituted cycloalkyl, unsubstituted or substituted cycloalkyl containing at least one heteroatom, unsubstituted or substituted aromatic ring, and unsubstituted or substituted aromatic ring containing at least one heteroatom,
(b) collecting the reactor effluent of step (a); and
(c) contacting the collected effluent with the base catalyst at a temperature of above 200° C.

27. The process of claim 26 wherein steps (b) and (c) are repeated from about 1 to about 10 times.

* * * * *